United States Patent [19]

Ichikawa et al.

[11] Patent Number: 5,374,625
[45] Date of Patent: Dec. 20, 1994

[54] ADENINE AND GUANINE DERIVATIVES FOR THE TREATMENT OF HEPATITIS VIRUS INFECTIONS

[75] Inventors: Yuh-ichiro Ichikawa; Hiroshi Akaba, both of Tokyo; Yuka Sugawara, Kawaguchi; Akira Shiozawa, Omiya; Kenichi Matsubara, Suita; Takemitsu Nagahata, Takasaki; Hiroo Hoshino, Maebashi; Jun-ichi Seki, Takasaki, all of Japan

[73] Assignee: Nippon Kayaku Kabushiki Kaisha, Tokyo, Japan

[21] Appl. No.: 731,459

[22] Filed: Jul. 17, 1991

[30] Foreign Application Priority Data

Jul. 24, 1990 [JP] Japan .................................. 2-193957

[51] Int. Cl.$^5$ ...................... A01N 43/04; A61K 31/70; C07H 19/00
[52] U.S. Cl. ........................................ 514/43; 514/45; 514/46; 514/49; 536/22.1
[58] Field of Search ..................... 514/44, 43, 45, 46, 514/49; 536/26, 22.1; 544/277, 264, 265

[56] References Cited

U.S. PATENT DOCUMENTS 4,383,114 5/1983 Vince .
4,988,703 1/1991 Norbeck et al. .

FOREIGN PATENT DOCUMENTS 0335355 10/1989 European Pat. Off. .
0358154 3/1990 European Pat. Off. .
0366059 5/1990 European Pat. Off. .

OTHER PUBLICATIONS

The Journal of Antibiotics, vol. XLII, No. 4, 1989 pp. 644–646.

Antimicrobial Agents and Chemotherapy, vol. 32, No. 7, 1988, pp. 1053–1056.
Medical Research Review vol. 6, No. 1, pp. 1–40 (1986).
Journal of the Chemical Society, Chemical Communications, No. 24: 1989, pp. 1919–1921; Ichikawa et al., "Enantio- and Diastereo-Selective Synthesis of Carbocyclic ...".
The Journal of Antibiotics, vol. XLII, No. 12, Dec. 1989, pp. 1854–1859; Nishiyama et al.: "Anti–Herpes Virus Activity of Carbocyclic Oxetanocin ...".
Chemical and Pharmaceutical Bulletin, vol. 38, No. 1, Jan. 1990, pp. 288–290. Katagiri et al.: "Highly Stereoselective Synthesis of Carbocyclic Analogues ...".

*Primary Examiner*—Elizabeth C. Weimar
*Assistant Examiner*—Deborah Crouch
*Attorney, Agent, or Firm*—Nields & Lemack

[57] ABSTRACT

A novel nucleic acid derivative represented by the following general formula (I) and physiologically acceptable salt thereof which are expected to have an antiviral activity:

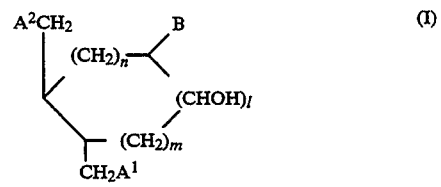

wherein B represents a nucleic acid base derivative; $A^1$ and $A^2$ represent, independently of each other, $OR^1$ or $OCOR^1$; $R^1$ represents a hydrogen atom, a substituted or unsubstituted alkyl group or a substituted or unsubstituted aryl group; l represents a number of 0 or 1; and m and n each represents an integer of 0–2; provided that when l and m are 0, n is 0 or 2.

3 Claims, No Drawings

ADENINE AND GUANINE DERIVATIVES FOR THE TREATMENT OF HEPATITIS VIRUS INFECTIONS

FIELD OF THE INVENTION

This invention relates to novel nucleic acid derivatives expectedly useful as medical drugs such as antiviral drug, carcinostatic agent and the like.

BACKGROUND OF THE INVENTION

In the field of nucleic acid-related substances, there are known many substances having an antiviral activity or a carcinostatic activity, and some of them are clinically used as useful medical drugs. For example, as antiviral agent, vidarabine [M. Privat de Garilhe and J. de Rubber, C. R. Acad. Soc. D (Paris) 259, 2725 (1964)], aciclovil [G. B. Elion et al., Proc. Natl. Acad. Sci, USA, 74, 5716 (1977)], azidothymidine [H. Mitsuya et al., Proc. Natl. Acad. Sci. USA, 82, 7096 (1985)], etc. are known. As carcinostatic agent, 5-fluorouracil, cytosine arabinoside, etc. are known.

Apart from the above, it is also known that nucleic acid derivatives represented by the following formula have an antiviral activity [Journal of Antibiotics (J.A.) Vol. XLII, No. 12, 1989, pp. 1854-1859; Antimicrob. Agents Chemother. Vol. 32, No. 7, 1988, pp. 1053-1056; J.A., Vol. XLII, No. 4, 1989, pp 644-646]:

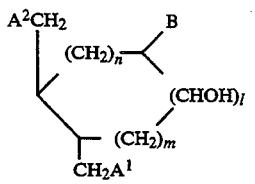

wherein B' represents adenine or guanine and X represents oxygen atom or methylene.

It is an object of this invention to develop novel nucleic acid derivatives which are expected to have an antiviral activity.

SUMMARY OF THE INVENTION

This invention relates to novel nucleic acid derivatives represented by the following general formula (I) and physiologically acceptable salts thereof:

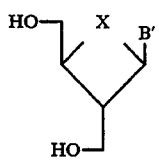

wherein B represents a nucleic acid base derivative, $A^1$ and $A^2$ independently represent $OR^1$ or $OCOR^1$, $R^1$ represents a hydrogen atom, a substituted or unsubstituted alkyl group or a substituted or unsubstituted aryl group, represents a number of 0 or 1, and m and n represent an integer of 0 to 2, provided that when l and m are 0, n is 0 or 2.

DETAILED DESCRIPTION OF THE INVENTION

In general formula (I), examples of the nucleic acid base derivatives represented by B include purine bases, pyrimidine bases and these bases protected by a protecting group. Examples of said purine base include compounds represented by the following formulas:

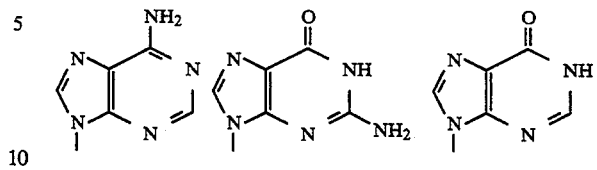

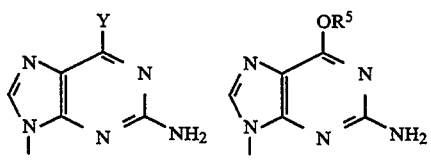

wherein Y represents hydrogen, amino group, or halogen such as chlorine, bromine, fluorine and the like and $R^5$ represents an alkyl group such as methyl group, ethyl group, butyl group, methoxyethyl group, benzyl group or the like. Examples of said pyrimidine group include compounds represented by the following formulas:

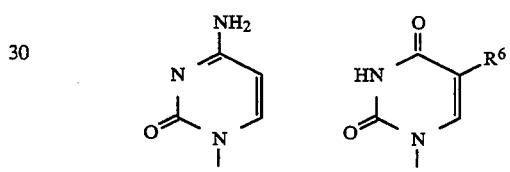

wherein $R^6$ represents hydrogen, alkyl group such as methyl, ethyl, butyl, benzyl and the like, vinyl group such as 2-bromovinyl, 2-iodovinyl and the like, or halogen such as fluorine, chlorine, bromine and iodine.

Examples of the substituted or unsubstituted alkyl group include straight or branched chain alkyl groups such as methyl group, ethyl group, octyl group, octadecyl group and the like, alkyl groups into which a hydroxyl group is introduced such as hydroxyethyl group and the like, alkyl groups into which an amino group is introduced such as dimethylaminopropyl group, 1,4-dihydro-1-methylpyridyl group and the like, alkyl groups into which an aromatic ring is introduced such as benzyl group, p-methoxybenzyl group and the like, etc. Examples of said substituted or unsubstituted aryl group include phenyl group, p-methoxyphenyl group, o-chlorophenyl group and the like.

Examples of said physiologically acceptable salt include salts of alkali metals such as sodium, potassium and the like, salts of alkaline earth metals such as calcium, magnesium and the like, ammonium salts, substituted ammonium salts, salts of mineral acids such as hydrochloric acid, sulfuric acid, nitric acid and the like, and salts of organic acids such as acetic acid, fumaric acid, maleic acid, tartaric acid, methanesulfonic acid and the like.

Among the compounds of this invention represented by general formula (I), compounds represented by the following formula:

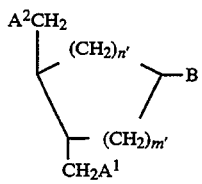

(I)

wherein m' represents a number of 0 or 2, n' represents a number of 1 or 2, and B, $A_1$ and $A_2$ are as defined above, provided that when m' is 0, n' is 2 and when m' is 2, n' is 1, are preferable. Concrete examples of the preferable compound include the compounds of Example Nos. 5, 16 and 21. Among these preferable compounds, the compounds represented by the following formula:

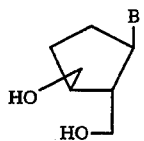

are particularly preferable. As concrete example of the particularly preferable compound, the compound of Example 5 can be referred to.

Concrete examples of the compound represented by general formula (I) are shown below. All the isomers, optically active isomers and racemic mixtures of these compounds are also included in the scope of this invention. Salts of these compounds are not shown herein.

1. 9-[2,3-Bis( hydroxymethyl)-1-cyclopropyl]-adenine,
2. 9-[2,3-Bis( hydroxymethyl)-1-cyclopropyl]-guanine,
3. 9-[2,3-Bis( hydroxymethyl)-1-cyclopropyl]-hypoxanthine,
4. 2-Amino-9-[2,3-bis(hydroxymethyl)-1-cyclopropyl]-purine,
5. 2-Amino-9-[2,3-bis(hydroxymethyl)-1-cyclopropyl]-6-chloropurine,
6. 2,6-Diamino-9-[2,3-bis(hydroxymethyl)-1-cyclopropyl]-purine,
7. 1-[2,3-Bis(hydroxymethyl)-1-cyclopropyl]-2,4-(1H,3H)-pyrimidinedione,
8. 1-[2,3-Bis(hydroxymethyl)-1-cyclopropyl]-5-methyl-2,4(1H,3H)-pyrimidinedione,
9. 1-[2,3-Bis(hydroxymethyl)-1-cyclopropyl]-5-fluoro-2,4(1H,3H)-pyrimidinedione,
10. 1-[2,3-Bis(hydroxymethyl)-1-cyclopropyl]-5-iodo-2,4(1H,3H)-pyrimidinedione,
11. 1-[2,3-Bis(hydroxymethyl)-1-cyclopropyl]-5-(2-bromovinyl)-2,4(1H,3H)-pyrimidinedione,
12. 4-Amino-1-[2,3-bis(hydroxymethyl)-1-cyclopropyl]-2(1H)-pyrimidinone,
13. 9-[2,3-Bis(hydroxymethyl)-1-cyclopentyl]-adenine,
14. 9-[2,3-Bis(hydroxymethyl)-1-cyclopentyl]-guanine,
15. 9-[2,3-Bis(hydroxymethyl)-1-cyclopentyl]-hypoxanthine,
16. 2-Amino-9-[2,3-bis(hydroxymethyl)-1-cyclopentyl]-purine,
17. 2-Amino-9-[2,3-bis(hydroxymethyl-1-cyclopentyl]-6-chloropurine,
18. 2,6-Diamino-9-[2,3-bis(hydroxymethyl)-1-cyclopentyl]-purine,
19. 1-[2,3-Bis(hydroxymethyl)-1-cyclopentyl]-2,4-(1H,3H)-pyrimidinedione,
20. 1-[2,3-Bis(hydroxymethyl)-1-cyclopentyl]-5-methyl-2,4(1H,3H)-pyrimidinedione,
21. 1-[2,3-Bis(hydroxymethyl)1-cyclopentyl]-5-fluoro-2,4(1H,3H)-pyrimidinedione,
22. 1-[2,3-Bis(hydroxymethyl)-1-cyclopentyl]-5-iodo-2,4(1H,3H)-pyrimidinedione,
23. 1-[2,3-Bis(hydroxymethyl)-1-cyclopentyl]-5-(2-bromovinyl)-2,4(1H,3H)-pyrimidinedione,
24. 4-Amino-1-[2,3-bis(hydroxymethyl)-1-cyclopentyl]-2(1H)-pyrimidinone,
25. 9-[3,4-Bis(hydroxymethyl)-1-cyclopentyl]-adenine,
26. 9-[3,4-Bis(hydroxymethyl)-1-cyclopentyl]-guanine,
27. 9-[3,4-Bis(hydroxymethyl)-1-cyclopentyl]-hypoxanthine,
28. 2-Amino-9-[3,4-bis(hydroxymethyl)-1-cyclopentyl]-purine,
29. 2-Amino-9-[3,4-bis(hydroxymethyl)-1-cyclopentyl]-6-chloropurine,
30. 2,6-Diamino-9-[3,4-bis(hydroxymethyl)-1-cyclopentyl]-purine,
31. 1-[3,4-Bis(hydroxymethyl)-1-cyclopentyl]-2,4-(1H,3H)-pyrimidinedione,
32. 1-[3,4-Bis(hydroxymethyl)-1-cyclopentyl]-5-methyl-2,4(1H,3H)-pyrimidinedione,
33. 1-[3,4-Bis(hydroxymethyl)-1-cyclopentyl]-5-fluoro-2,4(1H,3H)-pyrimidinedione,
34. 1-[3,4-Bis(hydroxymethyl)-1-cyclopentyl]-5-iodo-2,4(1H,3H)-pyrimidinedione,
35. 1-[3,4-Bis(hydroxymethyl)-1-cyclopentyl]-5-(2-bromovinyl)-2,4(1H,3H)-pyrimidinedione,
36. 4-Amino-1-[3,4-bis(hydroxymethyl)-1-cyclopentyl]-2(1H)-pyrimidinone,
37. 9-[3,4-Bis(hydroxymethyl)-1-cyclohexyl]-adenine,
38. 9-[3,4-Bis(hydroxymethyl)-1-cyclohexyl]-guanine,
39. 9-[3,4-Bis(hydroxymethyl)-1-cyclohexyl]-hypoxanthine,
40. 2-Amino-9-[3,4-Bis(hydroxymethyl)-1-cyclohexyl]-purine,
41. 2-Amino-9-[3,4-Bis(hydroxymethyl)-1-cyclohexyl]-6-chloropurine,
42. 2,6-Diamino-9-[3,4-bis(hydroxymethyl)-1-cyclohexyl]-purine,
43. 1-[3,4-Bis(hydroxymethyl)-1-cyclohexyl]-2,4-(1H,3H)-pyrimidinedione,
44. 1-[3,4-Bis(hydroxymethyl)-1-cyclohexyl]-5-methyl-2,4(1H,3H)-pyrimidinedione,
45. 1-[3,4-Bis(hydroxymethyl)-1-cyclohexyl]-5-fluoro-2,4(1H,3H)-pyrimidinedione,
46. 1-[3,4-Bis(hydroxymethyl)-1-cyclohexyl]-5-iodo-2,4(1H,3H)-pyrimidinedione,
47. 1-[3,4-Bis(hydroxymethyl)-1-cyclohexyl]-5-(2-bromovinyl)-2,4(1H,3H)-pyrimidinedione,
48. 4-Amino-1-[3,4-bis(hydroxymethyl)-1-cyclohexyl]-2(1H)-pyrimidinone,
49. 9-[4,5-Bis(hydroxymethyl)-2-hydroxy-1-cyclohexyl]-adenine,
50. 9-[4,5-Bis(hydroxymethyl)-2-hydroxy-1-cyclohexyl]-guanine,
51. 9-[4,5-Bis(hydroxymethyl)-2-hydroxy-1-cyclohexyl]-hypoxanthine, 52. 2-Amino-9-[4,5-bis(hydroxymethyl)-2-hydroxy-1-cyclohexyl]-purine,
53. 2-Amino-9-[4,5-bis(hydroxymethyl)-2-hydroxy-1-cyclohexyl]-6-chloropurine,
54. 2,6-Diamino-9-[4,5-bis(hydroxymethyl)-2-hydroxy-1-cyclohexyl]-purine,
55. 1-[4,5-Bis(hydroxymethyl)-2-hydroxy-1-cyclohexyl]-2,4(1H,3H)-pyrimidinedione,
56. 1-[4,5-Bis(hydroxymethyl)-2-hydroxy-1-cyclohexyl]-5-methyl-2,4(1H,3H)-pyrimidinedione,
57. 1-[4,5-Bis(hydroxymethyl)-2-hydroxy-1-cyclohexyl]-5-fluoro-2,4(1H,3H)-pyrimidinedione,
58. 1-[4,5-Bis(hydroxymethyl)-2-hydroxy-1-cyclohexyl]-5-iodo-2,4(1H,3H)-pyrimidinedione,
59. 1-[4,5-Bis(hydroxymethyl)-2-hydroxy-1-cyclohexyl]-5-(2-bromovinyl)-2,4(1H,3H)-pyrimidinedione,
60. 4-Amino-1-[4,5-bis(hydroxymethyl)-2-hydroxy-1-cyclohexyl]-2(1H)-pyrimidinone.

The compounds of this invention represented by general formula (I) can be produced by, for example, reacting a compound represented by the following general formula (II) or (III):

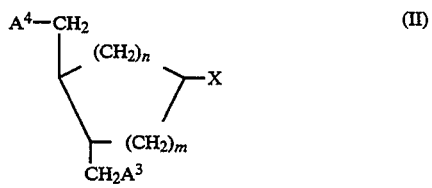
(II)

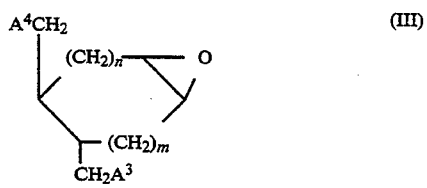
(III)

wherein X represents a leaving group, $A^3$ and $A^4$, independently of each other, represent $OR^3$ or $OCOR^1$, $R^1$ represents a hydrogen atom, a substituted or unsubstituted alkyl group or a substituted or unsubstituted aryl group, $R^3$ represents a hydrogen atom, a protecting group, a substituted or unsubstituted alkyl group or a substituted or unsubstituted aryl group, and m and n each represents an integer of 0 to 2, provided than when m is 0, n is 0 or 2, with a nucleic acid base derivative in a solvent to obtain a compound represented by the following formula (V):

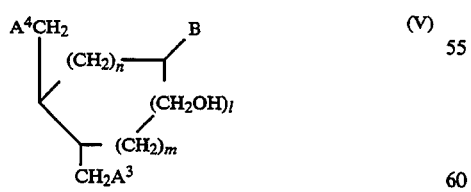
(V)

wherein B is a nucleic acid base derivative and $A^3$, $A^4$, l, m and n are as defined above, followed by, when the compound of formula (V) has a protecting group or when l in formula (V) is 1, eliminating the protecting group or the hydroxyl group of l, if desired.

As the compound of formula (II), compounds represented by the following formula:

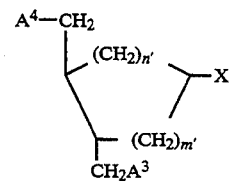

wherein m', n', X, $A^3$ and $A^4$ are as defined above, are preferable, and compounds represented by the following formula:

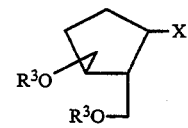

wherein X and $R^3$ are as defined above, are more preferable.

Examples of the leaving group X in general formula (II) include readily eliminable substituents such as sulfonyloxy groups (e.g. methanesulfonyloxy group, p-toluenesulfonyloxy group, trifluoromethanesulfonyloxy group and the like), halogen atoms (e.g. chlorine, bromine, iodine and the like), etc.

The protecting group is not critical, so far as it is conventionally used as a protecting group. The protecting groups which can be used in this invention include ester type protecting groups such as acyl groups (e.g. acetyl, benzoyl and the like), carbamoyl groups (e.g. dimethylcarbamoyl, diphenylcarbamoyl and the like), ether type protecting groups such as silyl groups (e.g. t-butyldimethylsilyl, t-butyldiphenylsilyl and the like), ($C_1$–$C_4$ alkoxy)-($C_1$–$C_4$ alkyl) groups (e.g. methoxymethyl and the like), tetrahydropyranyl group, and substituted methyl groups having one or more substituted or unsubstituted phenyl substituent(s) (e.g. benzyl, 4-methoxybenzyl, trityl and the like).

Examples of said nucleic acid base derivative include purine bases such as adenine, hypoxanthine, guanine, 2-amino-6-chloropurine, 2-aminopurine, 2,6-diaminopurine, 2-amino-6-ethoxypurine, 2-amino-6-(2-methoxyethoxy)-purine and the like. These compounds may optionally have a protecting group. Thus, as examples of the nucleic acid base derivative, compounds represented by the following general formula (VI):

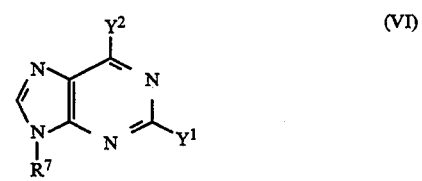
(VI)

wherein $R^7$ represents hydrogen or a protecting group, $Y^1$ represents hydrogen or $NHR^7$, $Y^2$ represents $Y^1$ or $OR^8$ and $R^8$ represents hydrogen or a protecting group, can be referred to.

Herein, as said protecting group, the above-mentioned protecting groups can be referred to. The protecting group for $R^8$ also include, in addition to the above-mentioned ones, groups conventionally used as protecting group of nucleic acid base, such as benzyl group, lower alkyl groups having 1-5 carbon atoms (e.g. butyl group and the like), (C₁-C₅ alkoxy)-(C₁-C₅ alkyl) groups (e.g. methoxyethyl group and the like), etc. Further, pyrimidine bases such as uracil, thymine, cytosine, 5-iodouracil, 5-fluorouracil, 5-(2-bromovinyl-)uracil and the like are also included. These compounds may optionally have a protecting group. Examples of the pyrimidine base include compounds represented by the following general formula (VII):

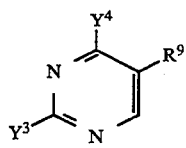

wherein $Y^3$ represents $OR^7$, $Y^4$ represents $Y^3$ or $NHR^7$, $R^7$ represents hydrogen or a protecting group and $R^9$ represents hydrogen, alkyl group such as methyl, ethyl, butyl, and the like, benzyl, vinyl group such as 2-bromovinyl, 2-iodovinyl and the like, and halogen such as fluorine, chlorine, bromine and iodine.

In the reaction between a compound represented by general formula (II) or (III) and a nucleic acid base such as a compound represented by general formula (VI) or (VII), the quantitative ratio between the compound of general formula (II) or (III) and the compound of general formula (VI) or (VII) is preferably about 0.5 to 10 equivalents of the latter per one equivalent of the former, preferably about 1 to 5 equivalents of the latter per one equivalent of the former. The reaction is carried out in the presence or absence of a basic catalyst, in a solvent, at a temperature ranging from 0° C. to refluxing temperature of the solvent, preferably at a temperature ranging from neighborhood of room temperature to about 170° C.

Examples of the basic catalyst include alkali metal hydroxides such as sodium hydroxide, potassium hydroxide and the like, alkali metal salts such as sodium carbonate, lithium carbonate, potassium carbonate and the like, alkali metal hydrides such as lithium hydride, sodium hydride and the like, etc. Said basic catalyst used, for example, in an amount of 0 to 2 equivalents, preferably about 0.1 to 2 equivalents, and more preferably about 0.3 to 1.2 equivalents, per one equivalent of the compound of general formula (VI) or (VII).

As the solvent, aprotic solvents are preferable, and aprotic polar solvents are more preferable. Examples of the more preferable aprotic polar solvent include N,N-dimethylformamide (DMF), dimethyl sulfoxide (DMSO), 1,3-dimethyl-2-imidazolidinone (DMI), hexamethylphosphoric triamide (HMPA) and the like.

When the compound of formula (V) formed by reaction between a compound represented by general formula (II) or (III) and a nucleic acid base derivative has a protecting group, removal of the protecting group can be achieved by adopting an appropriate protecting group-removing agent or an appropriate protecting group-removing method which agents and methods should be varied appropriately depending on the kind of the protecting group. For example, an alkali such as sodium hydroxide, sodium methylate, ammonia and the like, an acid such as hydrochloric acid, sulfuric acid and the like, a fluorine-containing agent such as tetrabutylammonium fluoride and the like, or a method such as hydrogenolysis and the like is adopted.

When the hydroxyl group, in a number of l, is to be removed from a compound of formula (V) wherein l is 1, the hydroxyl group is usually removed reductively.

For example, the hydroxyl group is converted to a reductively eliminable group such as a thiocarbonyl derivative, and then the latter is eliminated by the use of a reductant such as tributyltin hydride and the like.

Among the compounds represented by general formula (II), the compounds represented by the following general formula (IIa) can be produced according to the following reaction scheme (1), for example:

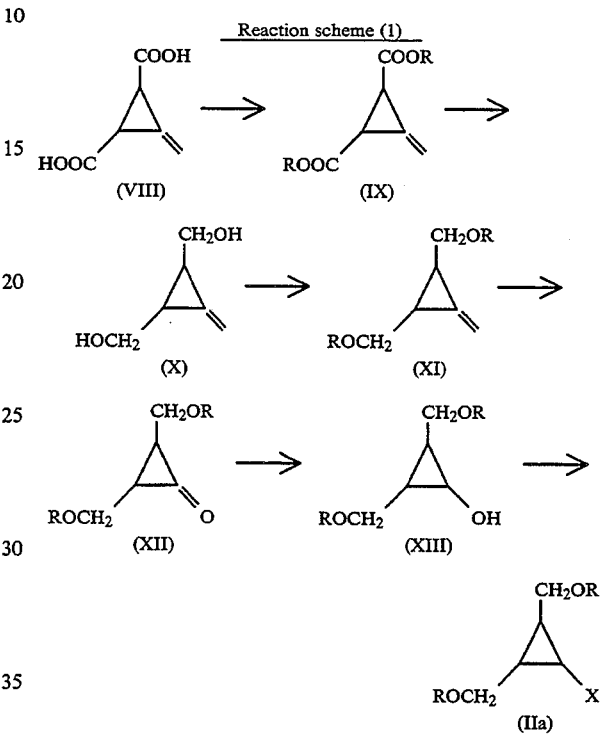

wherein R represents alkyl group or $R^3$ of general formula (II). Thus, a compound (VIII) disclosed in literature [F. Feist, Chem. Ber. 26, 750 (1893)] is converted to an ester and then the ester is reduced with a metal hydride such as lithium aluminum hydride, di(isobutyl-)aluminum hydride, sodium borohydride, lithium borohydride, diborane and the like to obtain an alcohol represented by (X). Then, the hydroxyl group of compound (X) is protected to obtain a compound represented by general formula (XI). Its double bond is oxidized by ozone oxidation, osmium tetraoxide oxidation in the presence of sodium periodate, etc. to obtain a ketone represented by general formula (XII). Then, the latter is reduced with a metal hydrogen complex such as lithium aluminum hydride, lithium tri(t-butoxy)aluminum hydride, sodium borohydride, sodium cyanoborohydride, lithium tri(s-butyl)borohydride, lithium borohydride and the like or a metal hydride such as diisobutylaluminum hydride, diborane and the like as a reductant, in a solvent selected from hydrocarbon solvents such as pentane, hexane, heptane, petroleum ether, benzene, toluene, ethylbenzene and the like, halogenated hydrocarbon solvents such as methylene chloride, chloroform and the like, ethereal solvents such as ether, tetrahydrofuran and the like, alcoholic solvents such as methanol, ethanol and the like, water, and mixture thereof, at a reaction temperature of −100° C. to 50° C., preferably about −80° C. to about 30° C., to obtain a compound represented by general formula (XIII). Then, the secondary hydroxyl group of the compound (XIII) thus obtained is converted to a leaving group, whereby a compound represented by general formula (IIa) can be obtained.

Among the compounds represented by general formula (II), compounds represented by the following general formula (IIb) or (IIc) can be produced according to, for example, the following reaction scheme (2):

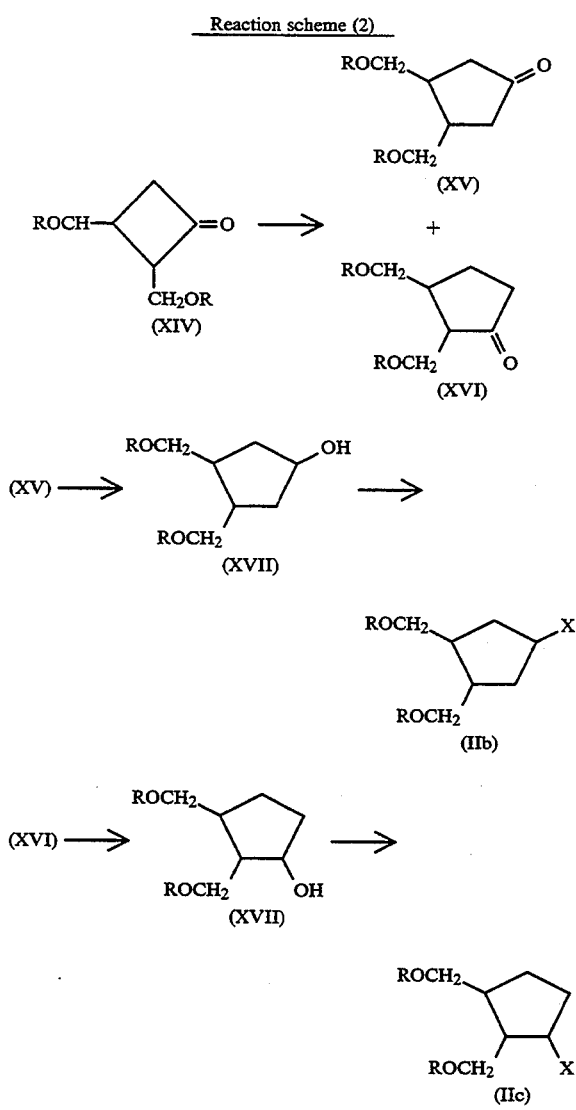

wherein R represents $R^3$ of general formula (II). Thus, cyclobutanone (XIV) disclosed in literature [Y. Ichikawa et al., J. Chem. Soc., Chem. Commun., 1919 (1989)] is reacted with diazomethane, trimethylsilyldiazomethane or the like to enlarge its ring, whereby (XIV) can be converted to a cyclopentanone derivatives (XV) and (XVI). Compounds (XV) and (XVI) are separately reduced and thereafter their secondary hydroxyl group is converted to a leaving group to obtain compounds represented by general formula (IIb) and (IIc), respectively.

Among the compounds represented by general formula (II), the compounds represented by the following general formula (IId) can be produced by, for example, according to the following reaction scheme (3):

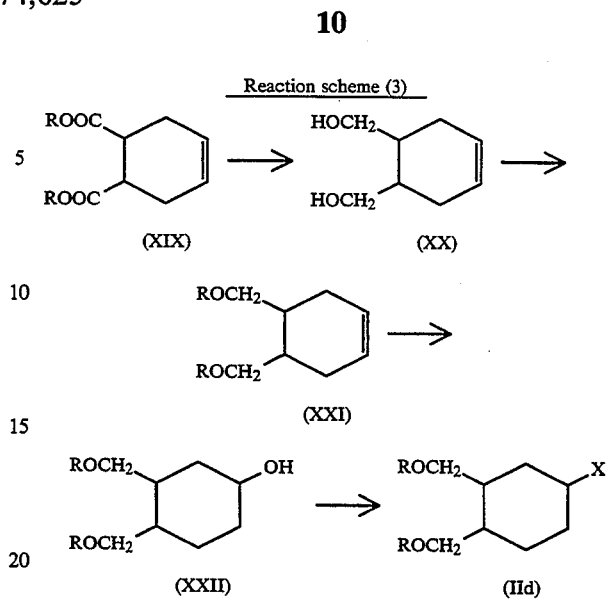

wherein R represents alkyl group or $R^3$ of general formula (II). Thus, a compound of formula (XIX) which can directly be derived from a compound disclosed in literature [N. Narasaka et al., J. Am. Chem. Soc., 111, 5340 (1989)] is reduced to obtain an alcohol represented by formula (XX). Then, the hydroxyl group of compound (XX) is protected to obtain a compound represented by general formula (XXI). Double bond part of XXI is subjected to a hydroboration-oxidation reaction by the use of, for example, diborane, 9-BBN, disiamylborane or the like to obtain an alcohol represented by general formula (XXII). By converting the secondary hydroxyl group of this compound to a leaving group, a compound represented by general formula (IId) can be obtained.

Among the compounds represented by general formula (III), the compounds represented by the following general formula (IIIa) can be produced, for example, according to the following reaction scheme (4):

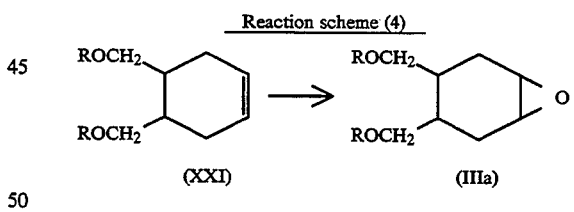

wherein R represents $R^3$ or $R^4$ of general formula (II). Thus, those can be obtained by epoxidizing a compound represented by general formula (XXI) with a peracid such as m-chloroperbenzoic acid or the like.

The following Exaperiment Examples demonstrate that the compounds of this invention exhibit a strong antiviral activity.

EXPERIMENT EXAMPLE 1

Antiviral activity against Herpes simplex virus (HSV-1) which is a DNA virus was tested by the following method.

(Method 1)

Vero cells (originated from kidney cells of African Green Monkey) were cultured in MEM medium supplemented with 10% fetal bovine serum. One hundred μl of cell suspension (200,000 cells/ml) was plated into 96 wells plates (COSTAR) and cultured for 24 hours so that the culture became confluent. The medium was drawn, and cells were infected with HSV-1 virus for one hour. After drawing the virus fluid, cells were cultured for about 72 hours in a fresh medium containing test samples. The survived cells were stained with Neutral Red solution and absorbance at a wavelength of 546 nm ($A_{546}$) was measured to evaluate the cytopathic effect (CPE).

CPE inhibition (%) was calculated as follows:

$$\text{CPE inhibition (\%)} = 100 \times \left[ 1 - \frac{A_{546}(\text{drug treatment}) - A_{546}(\text{virus control})}{A_{546}(\text{cell alone}) - A_{546}(\text{virus control})} \right]$$

Sample concentration required for 50% inhibition of the CPE was calculated as $IC_{50}$ (μg/ml).

The results are summarized in Table 1.

EXPERIMENTAL EXAMPLE 2

Antiviral activity against Human Immonodeficiency Virus (HIV) belonging to RNA virus was examined by the following method:

MT-4 cells ($0.5 \times 10^5$) in 0.5 ml of RPMI 1640 culture medium were seeded into 48-well plates, and 50 μl of test compounds were added to various concentrations. The cells were incubated at 37° C. for 2 hours in 5% (v/v) carbondioxide incubator. Then, 50 μl of the HTLV-III$_B$ strain of HIV ($2.5 \times 10^5$ to $5 \times 10^5$ PFU/ml) was inoculated onto the cells. After 4 days, a part of the cells were applied onto a slide glass and immobilized with acetone. The percentages of HIV antigen-positive MT-4 cells were determined by indirect immunofluorescence assay. As the primary antibody, serum of AIDS patients was used. As the secondary antibody, FITC-labelled anti-human IgG was used.

The results are summarized in Table 1.

TABLE 1

| Compound | $IC_{50}$ (μg/ml) | |
|---|---|---|
| (Example No.) | HSV-1 | HIV |
| 13 | | 55 |
| 16 | | 4.5 |
| 18 | 45.9 | |
| 21 | 2.77 | |

EXPERIMENTAL EXAMPLE 3

Antiviral activity against hepatitis B virus (HBV) which is a DNA virus was tested by the following method.

The test was done by using a cell line, HB611, that was established by transfection and continuously produces HBV-like particles [Proc. Natl. Acad. Sci. USA, 84, 444-449, 1987]. HB611 cells were maintained in Dulbecco's modified Eagle medium (Gibco) supplemented with fetal bovine serum (Gibco), 100 μg/ml of streptomycin, IU ml of benzyl penicillin (Gibco) and 200 μg/ml of geneticin (Gibco) at 37° C. in 5% CO$_2$-95% air.

The cells were seeded in 24-well plate (Corning) at a density of $3 \times 10^4$ cells/well, using 1.0 ml of the medium. After 2 days of incubation, the medium was replaced with the same medium containing the test compound. The cells were incubated for a further 15 days, during which time the medium containing the drug was exchanged every three days. The cells were then harvested and cellular DNA was prepared [Virology, 169, 213-216, 1989], and digested with restriction enzyme Hind III (Takara Shuzo Co., Ltd.). An aliquot (2-3 μg) was electrophoresed in 1.5% agarose gel, followed by blotting onto a nylon membrane Hybond-N+ according to Southern [J. Mol. Biol., 8, 503-517, 1975]. The filter was hybridized to random primed 32p labeled HBV DNA probe, and washed twice with 2× standard saline citrate containing 0.1% SDS at 65° C. for 30 min. It was then autoradiographed.

The results are shown in Table 2.

TABLE 2

| | Activity against hepatitis B virus | | |
|---|---|---|---|
| Compound | Concentration (μg/ml) | Viral DNA synthesis-inhibitory effect | Cytotoxicity |
| Example No. 5 | 100 | +++ | — |
| | 10 | +++ | — |
| | 1 | + | — |
| | 0.1 | — | — |

The results which was autoradiographed were analyzed using a densitometric analyzer (Shimadzu, Chromatoscana S930).

To quantitatively evaluate the inhibitory activity of the compounds, there were measured the band areas S, D, D2 (S, D1 and D2 represent intracellular free HBV DNA derived from replicative intermediates) and I (represents chromosomally integrated HBV DNA) by densitometric analyzer, and calculated the inhibition percentage as follows:

$$\text{Inhibition (\%)} = \left[ 1 - \frac{(S_{drug} + D1_{drug} + D2_{drug})/I_{drug}}{(S_{cont} + D1_{cont} + D2_{cont})/I_{cont}} \right] \times 100$$

Anti-HBV activity ID50, expressed as the drug concentration required for 50% inhibition of the viral DNA synthesis, was obtained by plotting the inhibition (%) vs drug concentration.

The results are shown in Table 3.

TABLE 3

| Compound | $ID_{50}$ (μg/ml) |
|---|---|
| Example No. 5 | 0.24 |

The compounds of this invention represented by general formula (I) have an antiviral activity. Accordingly, they are expected to be effectively usable against herpes labialis, herpes genitalis, herpes zoster, infections of herpes simplex virus-I and II (HSV-I, II), varicella zoster virus (VZV), cytomegalo virus (CMV) and Epstein-Barr virus (EBV) at the time of immuno-depression and many other viral diseases such as viral hepatitises caused by hepatitis B virus and hepatitis C virus, viral diseases of respiratory organs, viral diseases of digestive organs, AIDS, ATL and the like. Further, they are expected to be useful as a carcinostatic agent.

In putting to use the compounds of this invention obtained in the above-mentioned manner, they can be administered orally, intravenously and subcutaneously. Although their dose varies depending on the symptoms and age of patient to whom they are administered and the method of administration, it is usually 1 to 500 mg/kg/day. The compounds of this invention are administered in the form of a medical preparation prepared by mixing the compound with an appropriate carrier. As the form of the preparation, tablet, granule, fine granule, powder, capsule, injection, cream, suppository and the like can be adopted. The quantity of active ingredient contained in the preparation ranges from about 0.01% to about 99%.

Next, production of the compounds of this invention will be explained more concretely by way of the following examples.

EXAMPLE 1

Production of (2S,3S)-2,3-Bis(t-butyldiphenyl-silyloxymethyl)-1-cyclopentanone and (3S,4S)-3,4-Bis(t-butyldiphenylsilyloxymethyl)-1-cyclopentanone A solution of diazomethane (ca. 2 g) in ether (200 ml) was added to (2S,3S)-2,3-bis(t-butyldiphenylsilyloxymethyl)-1-cyclobutanone (12.14 g, 20 mmoles) synthesized according to a method disclosed in literature Y. Ichikawa et al., J. Chem. Soc. Chem. Commun., 1919 (1989)], and the resulting mixture was stirred at room temperature for one week. After distilling off the solvent from the reaction mixture under reduced pressure, the residue was purified by silica gel column chromatography (ethyl ether:n-hexane=1:10, v/v) to obtain (2S,3S)-2,3-bis(t-butyldiphenylsilyloxymethyl)-1-cyclopentanone (2.07 g, Yield 17%):
NMR (200 MHzFT, TMS, CDCl$_3$) δ:
0.98(9H, s),
1.02(9H, s),
1.79(1H, m),
2.05–2.50(4H, m),
2.65(1H, m),
3.52–3.68(2H, m),
3.80(1H, dd, J=4.3, 10.3 Hz),
4.04(1H, dd, J=3.6, 10.5 Hz),
7.25–7.47(12H, m),
7.55–7.68(8H, m),
and ( 3S, 4S ) -3,4-bis( t-butyldiphenylsilyloxymethyl)-1-cyclopentanone (2.63 g, Yield 21%):
NMR (200 MHzFT, TMS, CDCl$_3$) δ:
1.01(18H, s),
2.12–2.51(6H, m),
3.51–3.73(4H, m),
7.26–7.48(12H, m),
7.55–7.65(8H, m).

EXAMPLE 2

Production of (1S,2S,3S)-2,3-Bis(t-butyldiphenylsilyloxymethyl)-1-cyclopentanol and (1R,2S,3S)-2,3-bis(t-butyldiphenylsilyloxymethyl)-1-cyclopentanol In an atmosphere of argon gas, 1M solution of diisobutylaluminum hydride in toluene (2.7 ml, 2.7 mmoles) was slowly added at −78° C. to solution of (2S,3S)-2,3-bis-(t-butyldiphenylsilyloxymethyl)-1-cyclopentanone (1.40 g, 2.25 mmoles) in toluene (23 ml), and the resulting mixture was stirred at that temperature for 15 minutes. Then, 0.2M phosphate buffer solution (pH 7) was added to the reaction mixture and stirred for a while, after which an excessive amount of methylene chloride was added and the inorganic matter was filtered off. The filtrate was subjected to extraction with methylene chloride and an extract solution was dried on anhydrous sodium sulfate, and then the solvent was distilled off. The residue was purified by silica gel column chromatography (ethyl acetate: n-hexane=1:10, v/v) to obtain (1S,2S,3S)-2,3-bis(t-butyldiphenylsilyloxymethyl)-1-cyclopentanol (1,120 g, Yield 80%):
NMR (200 MHzFT, TMS, CDCl$_3$) δ:
0.96(9H, s),
1.05(9H, s),
1.34–2.18(6H, m),
2.90(1H, brs),
3.35–3.52(2H, m),
3.75(1H, dd, J=7.5, 10.5 Hz),
3.97(1H, dd, J=4.4, 10.4 Hz),
4.46(1H, diff. q),
7.25–7.46(12H, m),
7.52–7.71(8H, m).
and (1R,2S,3S)-2,3-bis(t-butyldiphenylsilyloxymethyl)-cyclopentanol (148 mg, Yield 11%):
NMR (200 MHzFT, TMS, CDCl$_3$) δ:
0.98(9H, s),
1.05(9H, s),
1.50–2.00(6H, m),
2.79(1H, brs),
3.51(2H, d, J=5.2 Hz),
3.56(1H, dd, J=8.5, 10.0 Hz),
3.86(1H, dd, J=4.9, 10.0 Hz),
4.12(1H, diff. q, J=6.1 Hz),
7.26–7.48(12H, m),
7.55–7.77(8H, m).

EXAMPLE 3

Production of (1S,2S,3S)-2,3-Bis(t-butyldiphenylsilyloxymethyl)-1-cyclopentyl methane-sulfonate At 0° C., methanesulfonyl chloride (0.20 ml, 2.6 mmoles) was added to a solution of (1S, 2S, 3S)-2,3-bis-(t-butyldiphenylsilyloxymethyl)-1-cyclopentanol (1.08 g, 1.73 mmoles) and triethylamine (0.44 ml, 3.2 mmoles) in methylene chloride (9 ml). After stirring the mixture at 0° C. for 15 minutes, 0.2M phosphate buffer (pH 7.0) was added to the reaction mixture and the mixture was subjected to extraction with ethyl ether. The ether extract solution was dried on anhydrous sodium sulfate and then the solvent was distilled off. The residue was purified by silica gel column chromatography (ethyl acetate:n-hexane=1:9, v/v) to obtain (1S,2S,3S)-2,3-bis-(t-butyldiphenylsilyloxymethyl)-1-cyclopentyl methanesulfonate (1.169 g, Yield 96%).
NMR (200 MHzFT, TMS, CDCl$_3$) δ:
0.97(9H, s),
1.04(9H, s),
1.56(1H, m),
1.78–2.22(5H, m),
2.92(3H, s),
3.42(2H, d, J=4.5 Hz),
3.77(2H, d, J=6.6 Hz),
5.29(1H, m),
7.23–7.47(12H, m),
7.53–7.70(8H, m).

EXAMPLE 4

Production of 9-[(1R,2R,3S)-2,3-Bis(t-butyldiphenylsilyloxymethyl)-1-cyclopentyl]-adenine In an atmosphere of argon gas, 60% sodium hydride (40 mg, 1.0 mmole) was added to a suspension of adenine (135 mg, 1.0 mmole) in DMF (7 ml). After stirring the mixture for one hour, (1S,2S,3S)-bis(t-butyldiphenylsilyloxymethyl)- 1-cyclopentyl methanesulfonate (350 mg, 0.5 mmole) was added to the reaction mixture, and the resulting mixture was stirred at 140° C. for 1.5 hours. After cooling the mixture, 0.2M phosphate buffer (pH 7) was added thereto and the product was extracted with ethyl acetate. The extract solution was washed with water, washed with saturated aqueous solution of sodium chloride and dried on anhydrous sodium sulfate, and then the solvent was distilled off. The residue was purified by silica gel column chromatography (methylene chloride: methanol=30:1 v/v) to obtain 9-[(1R,2R,3S)-2,3-bis(t-butyldiphenylsilyloxymethyl)-1-cyclopentyl]-adenine (140 mg, Yield 38%).

NMR (200 MHzFT, TMS, CDCl$_3$) δ:
- 0.93(9H, s),
- 1.04(9H, s),
- 1.86–2.00(2H, m),
- 2.02–2.38(3H),
- 2.53(1H, m),
- 3.59(2H, d, J=4.3 Hz),
- 3.65(1H, dd, J=5.5, 10.0 Hz),
- 3.73(1H, dd, J=5.5, 10.0 Hz),
- 4.89(1H, diff. q),
- 5.66(2H, brs),
- 7.19–7.44(12H, m),
- 7.44–7.55(4H, m),
- 7.59–7.69 (4H, m),
- 7.64(1H, s),
- 8.30(1H, s).

EXAMPLE 5

Production of 9-[(1R,2R,3S)-2,3-Bis(hydroxymethyl)-1-cyclopentyl]-adenine

4N-Hydrochloric acid/dioxane (0.17 ml, 0.68 mmole) was added to a solution of 9-[(1R,2R,3S)-2,3-bis-(t-butyldiphenylsilyloxymethyl)-1-cyclopentyl]-adenine (129 mg, 0.17 mmole) in methanol (1 ml). After stirring the mixture at room temperature overnight, solvent was distilled off from the reaction mixture under reduced pressure, after which water was added to the residue, ether-soluble material was removed therefrom, the residual solution was neutralized with 0.1N solution of sodium hydroxide, and solvent was distilled off therefrom. The residue was purified by Diaion HP-20 column chromatography (methanol concentration gradient) to obtain 9-[(1R,2R,3S)-2,3-bis(hydroxymethyl)-1-cyclopentyl]-adenine (43 mg, Yield 94%).

NMR (200 MHzFT, TMS, CD$_3$OD) δ:
- 1.74–2.02(2H, m),
- 2.02–2.31(3H, m),
- 22.40(1H, m),
- 3.57(2H, d, J=5.3 Hz),
- 3.69(2H, d, J=6.0 Hz),
- 4.78(1H, apparent q, J=8.6 Hz),
- 8.20(1H, s),
- 8.26(1H, s).

EXAMPLE 6

Production of 2-Amino-9-[(1R,2R,3S)-2,3-bis-(t-butyldiphenylsilyloxymethyl)-1-cyclopentyl]-6-(2-methoxyethoxy)purine In an atmosphere of argon gas, lithium hydride (8.4 mg, 1.06 mmoles) was added to a suspension of 2-amino-6-(2-methoxyethoxy)purine (221 mg, 1.06 mmoles) in DMF (7 ml). After stirring the mixture for one hour, (1S,2S,3S)-2,3-bis(t-butyldiphenylsilyloxymethyl)-1-cyclopentyl methanesulfonate (370 mg, 0.53 mmole) was added, and the resulting mixture was stirred at 140° C. for one hour. After cooling the mixture, 0.2M phosphate buffer (pH 7) was added, and the product formed was extracted with ethyl acetate. The extract solution was washed with water, washed with saturated aqueous solution of sodium chloride and dried on anhydrous sodium sulfate, and then the solvent was distilled off. The residue was purified by silica gel column chromatography (methylene chloride:methanol=50:1, v/v) to obtain 2-amino-9-[(1R,2R,3S)-2,3-bis(t-butyldiphenylsilyloxymethyl)-1-cyclopentyl]-6-(2-methoxyethoxy)-purine (124 mg, Yield 29%).

NMR (200 MHzFT, TMS, CDCl$_3$) δ:
- 0.97(9H, s),
- 1.04(9H, s),
- 1.76–1.95(2H, m),
- 1.97–2.20(2H, m),
- 2.20–2.48(2H, m),
- 3.43(3H, S),
- 3.54(2H, d, J=3.7 Hz ),
- 3.62(1H, dd, J=5.2, 10.2 Hz),
- 3.71(1H, dd, J=4.8, 10.2 Hz),
- 3.81(2H, t, J=5.1 Hz),
- 4.60(2H, brs),
- 4.65(2H, t, J=5.1 Hz),
- 4.81(1H, apparent q, J=8.5 Hz),
- 7.21–7.42(12H, m),
- 7.46(1H, s),
- 7.49–7.58(4H, m),
- 7.59–7.69(4H, m).

EXAMPLE 7

Production of 9-[(1R,2R,3S)-2,3-Bis(hydroxymethyl)-1-cyclopentyl]-guanine

4N-Hydrochloric acid/dioxane (0.13 ml, 0.52 mmole) was added to a solution of 2-amino-9-[(1R,2R,3S)-2,3-bis(t-butyldiphenylsilyloxymethyl)-1-cyclopentyl-6-(2-methoxyethoxy)purine (105 mg, 0.129 mmole) in methanol (1 ml). After stirring the mixture at room temperature overnight, the solvent was distilled off from the reaction mixture under reduced pressure, water was added, the ether-soluble material was removed thereform, and the solvent was distilled off. After adding 2N aqueous hydrochloric acid (3 ml) to the residue, the mixture was heated at 100° C. for one hour. After neutralizing the reaction mixture with 1N aqueous solution of sodium hydroxide, the mixture was subjected to Diaion HP-20 column chromatography (methanol concentration gradient) to obtain 9-[(1R,2R,3S)-2,3-bis(hydroxymethyl)-1-cyclopentyl] -guanine (29 mg, Yield 81%).

NMR (200 MHzFT, TMS, CD$_3$OD) δ:
- 1.72–1.90(2H, m),
- 1.90–2.37(4H, m),
- 3.52(2H, dd, J=5.5, 11.2 Hz),
- 3.59(2H, dd, J=4.6, 11.2 Hz),
- 3.66(2H, d, J=6.0 Hz),
- 4.59(1H, apparent q, J=8.6 Hz),
- 7.83(1H, s).

EXAMPLE 8

Production of
(4S,5S)-4,5-Bis(methoxycarbonyl)-1-cyclohexene

In an atmosphere of argon gas, a solution of (4S,5S)-5-methoxycarbonyl-4-(oxazolidin-2-on-3-yl)carbonyl-1-cyclohexene (8.50 g, 33.6 mmoles) disclosed in literature [N. Narasaka et al, J. Am. Chem. Soc., 111, 5340 (1989)] in methanol (50 ml) was added to 1M dimethoxymagnesium/methanol (168 ml, 168 mmoles), and the mixture was stirred at 0° C. for 15 minutes. Saturated aqueous solution of ammonium chloride was added to the reaction mixture, and the resulting mixture was extracted with toluene. The toluene extract solution was washed with saturated aqueous solution of sodium chloride and then the solvent was distilled off under reduced pressure. The residue was purified by silica gel column chromatography (ethyl acetate:n-hexane=1:9, v/v) to obtain (4S,5S)-4,5-bis(methoxycarbonyl)-1-cyclohexene (1.89 g, Yield 30%).

NMR (200 MHzFT, TMS, CDCl$_3$) δ:
- 2.07–2.31(2H, m),
- 2.33–2.55(2H, m),
- 2.76–2.97(2H, m),
- 3.70(6H, s),
- 5.70(2H, d, J=2.9 Hz).

EXAMPLE 9

Production of
(4S,5S)-4,5-Bis(hydroxymethyl)-1-cyclohexene

In an atmosphere of argon gas, an ethereal solution (10 ml) of (4S,5S)-4,5-bis(methoxycarbonyl)-1-cyclohexene (1.86 g, 9.4 mmoles) was slowly added at 0° C. to a suspension (100 ml) of lithium aluminum hydride (713 mg, 18.8 mmoles) in ether, and the resulting mixture was stirred at 0° C. for 2 hours. After adding a saturated aqueous solution of sodium sulfate to the reaction mixture and decomposing the excessive reductant, anhydrous sodium sulfate was added and the whole mixture was stirred for a while. After filtering off the inorganic matter and washing the mixture with hot isopropyl alcohol, the filtrate and the washings were united, and the solvent was distilled off therefrom under reduced pressure. The residue was purified by silica gel column chromatography (ethyl acetate:n-hexane=2:1, v/v) and then recrystallized from ethyl acetate-hexane mixture to obtain (4S,5S)4,5-bis(hydroxymethyl)-1-cyclohexene (1.09 g, Yield 82%).

NMR (200 MHzFT, TMS, CDCl$_3$) δ:
- 1.63–2.13(6H, m),
- 3.40(2H, brs),
- 3.58(2H, brdd, J=5.5, 10.1 Hz),
- 3.73(2H, brd, J=10.0 Hz),
- 5.66(2H, d, J=2.5 Hz).

A part of this compound was taken out and converted to (R)-MTPA ester according to the usual method [(R)-MTPACl, DMAP/pyr], and its 400 MHz NMR was observed. As the result, optical purity of this substance was 85–90% ee.

EXAMPLE 10

Production of
(4S,5S)-4,5-Bis(benzoyloxymethyl)-1-cyclohexene

Benzoyl chloride (2.0 ml, 17 mmoles) was slowly added to a solution of (4S,5S)-4,5-bis(hydroxymethyl)-1-cyclohexene (1.00 g, 7.0 mmoles) in pyridine (7 ml) while cooling the system with ice. The resulting mixture was stirred at 0° C. for one hour. After adding dimethylaminopropylamine (0.8 ml, 6.4 mmoles) to the reaction mixture and stirring it at that temperature for 15 minutes, water was added and the product formed was extracted with ethyl ether. The ether extract solution was washed successively with water, dilute hydrochloric acid and saturated aqueous solution of sodium chloride and then dried on anhydrous sodium sulfate. After distilling off the solvent under reduced pressure, the residue was purified by silica gel column chromatography (ethyl acetate:n-hexane=1:9, v/v) to obtain (4S,5S)-4,5-bis(benzoyloxymethyl)-1-cyclohexene (2.5 g, Yield 100%).

NMR (200 MHzFT, TMS, CDCl$_3$) δ:
- 1.95–2.40(6H, m),
- 4.41(4H, brd, J=3.9 Hz),
- 5.71(2H, s),
- 7.35–7.46(4H, m),
- 7.48–7.59(2H, m),
- 7.96–8.06(4H, m).

EXAMPLE 11

Production of
(3S,4S)-3,4-Bis(benzoyloxymethyl)-7-oxabicyclo[4.1.0-]heptane m-Chloroperbenzoic acid (777 mg, 4.5 mmoles) was added to a solution of (4S,5S)-4,5-bis(benzoyloxymethyl)-1-cyclohexene (1.05 g, 3.0 mmoles) in methylene chloride (6 ml) under cooling with ice. After stirring the mixture at room temperature for 2 hours, a saturated aqueous solution of sodium hydrogen sulfite was added to the reaction mixture and the excessive peracid was decomposed, after which a saturated aqueous solution of sodium hydrogen carbonate was added and the whole mixture was subjected to extraction with ethyl ether. The ether extract solution was washed with water and then with saturated aqueous solution of sodium hydrogen carbonate, and dried on anhydrous sodium sulfate. After distilling off the solvent therefrom under reduced pressure, the residue was purified by silica gel column chromatography (ethyl acetate:n-hexane=1:3, v/v) to obtain (3S,4S)-3,4-bis(benzoyloxymethyl)-7-oxabicyclo[4.1.0]heptane (1.025 g, Yield 93%).

NMR (200 MHzFT, TMS, CDCl$_3$) δ:
- 1.76–2.42(6H, m),
- 3.21–3.33(2H, m),
- 4.25–4.44(4H, m),
- 7.33–7.45(4H, m),
- 7.48–7.59(2H, m),
- 7.94–8.06(4H, m).

EXAMPLE 12

Production of
9-[(1R,2R,4S,5S)-4,5-bis-benzoyloxymethyl)-2-hydroxycyclohexyl]adenine In an atmosphere of argon gas, 60% sodium hydride (20 mg, 0.65 mole) was added to a suspension of adenine (202.5 mg, 1.34 mmoles) in anhydrous DMF (10 ml). After stirring the mixture at room temperature for one hour, (3S,4S)-3,4-bis(benzoyloxymethyl)-7-oxabicyclo-[4.1.0]heptane (245 mg, 0.67 mmole) was added and the resulting mixture was heated in an oil bath kept at 140° C. for 3 hours. After adding 0.2M phosphate buffer (pH 7.0) to the reaction mixture and stirring the mixture for a while, the mixture was subjected to extraction with ethyl acetate. After drying the extract solution on anhydrous sodium sulfate, the solvent was distilled off under reduced pressure, and the residue was purified by silica gel column chromatography (methylene chloride:methanol=50:1, v/v) to obtain 9-[(1R,2R,4S,5S)-4,5-bis(benzoyloxymethyl)-2-hydroxycyclohexyl]-adenine (161 mg, Yield 48%).

NMR (200 MHzFT, TMS, CDCl$_3$) δ:
- 1.83–2.35(4H, m),
- 2.43–2.62(2H, m),
- 2.73(1H, m),
- 4.37–4.75(6H, m),
- 6.09(2H, brs),
- 7.26–7.64(6H, m),
- 7.71(1H, s),
- 7.99–8.11(5H, m).

EXAMPLE 13

Production of 9-[(1R,2R,4S,5S)-4,5-Bis(hydroxymethyl)-2-hydroxycyclohexyl]-adenine Sodium methoxide (40 mg, 0.74 mmole) was added to a solution of 9-[(1R,2R,4S,5S)-4,5-bis(benzoyloxymethyl)-2-hydroxycyclohexyl]-adenine (185 mg, 0.37 mmole) in a solvent mixture consisting of anhydrous methanol (4 ml) and anhydrous THF (4 ml) under ice cooling. After stirring the resulting mixture at room temperature for 5 hours, the reaction mixture was neutralized with dilute hydrochloric acid, and the solvent was distilled off therefrom under reduced pressure. The residue was purified by Diaion HP-20 column chromatography (methanol concentration gradient) to obtain 9-[(1R,2R,4S,5S)-4,5-bis(hydroxymethyl)-2-hydroxycyclohexyl]-adenine (109 mg, Yield 100%).

NMR (200 MHzFT, TMS, CD$_3$CD) δ:
- 1.70(1H, m),
- 1.95–2.14 (4H, m),
- 2.43(1H, m),
- 3.64–3.86(4H, m),
- 4.25–4.49(2H, m),
- 8.186(1H, s),
- 8.191(1H, s).

EXAMPLE 14

Production of 9-[(1R,2R,4S,5S)-4,5-Bis(benzoyloxymethyl)-2-(phenoxythiocarbonyloxy)-cyclohexyl]-adenine In an atmosphere of argon gas, 9-[(1R,2R,4S,5S)-4,5-bis(benzoyloxymethyl)-2-hydroxycyclohexyl]-adenine (151 mg, 0.3 mmole) was dissolved into acetonitrile (5 ml), to which were then added 4-dimethylaminopyridine (75.1 mg, 0.62 mmole) and phenyloxythiocarbonyl chloride (57 μl, 0.33 mmole). After stirring the resulting mixture at room temperature for 24 hours. 0.1M aqueous solution of sodium hydrogen carbonate was added to the reaction mixture, and the mixture was subjected to extraction with ethyl acetate. The extract solution was washed with water and then with saturated aqueous solution of sodium chloride and dried on anhydrous sodium sulfate, and the solvent was distilled off under reduced pressure. The residue was purified by silica gel column chromatography (methylene chloride:methanol=50:1, v/v) to obtain 9-[(1R,2R,4S,5S)-4,5-bis(benzoyloxymethyl)-2-(phenoxythiocarbonyloxy)cyclohexyl]-adenine (109 mg, Yield 56.8%).

NMR (200 MHzFT, TMS, CDCl$_3$) δ:
- 2.02–2.32(2H, m),
- 2.48–2.75 (3H, m),
- 2.98(1H, m),
- 4.44–4.69(4H, m),
- 4.92(1H, m),
- 5.70(2H, brs),
- 6.23(1H, m),
- 6.80–6.92(2H, m),
- 7.18–7.64(9H, m),
- 7.85(1H, s),
- 8.01–8.12(4H, m),
- 8.33(1H, s).

EXAMPLE 15

Production of 9-[(1S,3S,4S)-3,4-Bis(benzoyloxymethyl)-cyclohexyl]-adenine

In an atmosphere of argon gas, 2,2'-azobisisobutyronitrile (5.3 mg, 0.03 mmole) and tributyltin hydride (5.3 mg, 0.032 mmole) was added to a solution of 9-[(1R,2R,4S,5S)-bis(benzoyloxymethyl)-2-(phenoxythiocarbonyloxy)-cyclohexyl]-adenine (103 mg, 0.16 mmole) in anhydrous toluene (4 ml). After stirring the mixture at room temperature for 20 minutes, the reaction was carried out at 75° C. for 3 hours. The solvent was distilled off from the reaction mixture under reduced pressure, and the residue was purified by silica gel column chromatography (methylene chloride:methanol=100:1, v/v) to obtain 9-[(1S,3S,4S)-3,4-bis(benzoyloxymethyl)-cyclohexyl]-adenine (26.0 mg, Yield 33.2%).

NMR (200 MHzFT, TMS, CDCl$_3$) δ:
- 1.80–2.63(8H, m),
- 4.54(4H, d, J=6.8 Hz),
- 4.80(1H, m),
- 5.84(2H, brs),
- 7.36–7.50(4H, m),
- 7.51–7.63(2H, m),
- 7.94(1H, s),
- 8.03(4H, d, J=8.1 Hz),
- 8.33(1H, s).

EXAMPLE 16

Production of 9-[(1S,3S,4S)-3,4-Bis(hydroxymethyl)-cyclohexyl]-adenine

Sodium methoxide (2.7 mg, 0.55 mole) was added to a solution of 9-[(1S,3S,4S)-3,4-bis(benzoyloxymethyl)-cyclohexyl]-adenine (25 mg, 0.05 mole) in anhydrous methanol (2 ml) under cooling with ice. After stirring the mixture at room temperature overnight, the reaction mixture was neutralized with dilute hydrochloric acid and the solvent was distilled off under reduced pressure. Then, ethyl ether and water were added to the residue, the ethyl ether layer was removed, and the water was distilled off. Then, the residue was purified by Diaion HP-20 column chromatography (methanol concentration gradient) to obtain 9-[(1S,3S,4S)-3,4-bis(hydroxymethyl)-cyclohexyl]-adenine (9.4 mg, Yield 66.2%).

NMR (200 MHzFT, TMS, DMSO-d$_6$) δ:
- 1.58–2.31(8H, m),
- 3.45–3.65(4H, m),
- 4.50(1H, m),
- 4.55(1H, t, J=5.3 Hz),
- 4.61(1H, t, J=5.3 Hz),
- 7.17(2H, brs),
- 8.13(1H, s),
- 8.25(1H, s).

EXAMPLE 17

Production of
2-Amino-9-[(1R,2R,4S,5S)-4,5-bis(benzoyloxymethyl)-2-hydroxycyclohexyl]-6-(2-methoxyethoxy)purine In an atmosphere of argon gas, lithium hydride (4.8 mg, 0.6 mmole) was added to a suspension of 2-amino-6-(2-methoxyethoxy)-purine (354.4 mg, 1.69 mmoles) in anhydrous DMF (15 ml). After stirring the mixture at room temperature for one hour, (3S,4S)-3,4-bis(benzoyloxymethyl)-7-oxabicyclo[4.1.0]-heptane (310.4 mg, 0.85 mmole) was added, and the reaction was further continued at 140° C. for 1.5 hours. Then, while cooling the reaction mixture, 0.2M phosphate buffer solution (pH 7.0) was added thereto and the mixture was stirred for a while, and then the mixture was subjected to extraction with ethyl acetate. The extract solution was washed with water, washed with saturated aqueous solution of sodium chloride and dried on anhydrous sodium sulfate, and then the solvent was distilled off under reduced pressure. The residue was purified by silica gel column chromatography to obtain 2-amino-9-[1R,2R,4S,5S)-4,5-bis(benzoyloxymethyl)-2-hydroxycyclohexyl]-6-(2-methoxyethoxy)-purine (320 mg, Yield 65.6%).

NMR (200 MHzFT, TMS, CDCl$_3$) δ:
1.80–2.32(4H, m),
2.41–2.65(2H, m),
2.94(1H, m),
3.37(3H, s),
3.74(2H, t, J=5.0 Hz),
4.20(1H, m),
4.38–4.90(7H, m),
5.02(2H, brs),
7.32–7.51(4H, m),
7.51–7.64(2H, m),
7.99–8.11 (5H, m).

EXAMPLE 18

Production of
9-[(1R,2R,4S,5S)-4,5-Bis(hydroxymethyl)-2-hydroxycyclohexyl]-guanine Sodium methoxide (36 mg, 0.67 mmole) was added to a solution of 2-amino-9-[(1R,2R,4S,5S)-4,5-bis(benzoyloxymethyl)-2-hydroxycyclohexyl]-6-(2-methoxyethoxy)-purine (190 mg, 0.33 mmole) in anhydrous methanol (3 ml) under cooling with ice. After stirring the mixture at room temperature for 5 hours, the reaction mixture was neutralized with dilute hydrochloric acid and the solvent was distilled off under reduced pressure. Then, ethyl ether and water were added to the residue, the ethyl ether layer was removed, and water was distilled off. Then, the residue was heated at 100° C. for one hour together with 2N aqueous hydrochloric acid (7 ml). The reaction mixture was neutralized with 1N solution of sodium hydroxide and then purified by Diaion HP-20 column chromatography (methanol concentration gradient) to obtain 9-[(1R,2R,4S,5S)-4,5-bis(hydroxymethyl)-2-hydroxycyclohexyl]-guanine (70 mg, Yield 69%).

NMR (200 MHzFT, TMS, DMSO-d$_6$) δ:
1.42(1H, m),
1.67–1.97(4H, m),
2.10(1H, m),
3.40–3.59(4H, m),
3.85–4.15(2H, m),
4.57(1H, t, J=5.2 Hz),
4.62(1H, t, J=5.1 Hz),
4.73(1H, d, J=4.8Hz),
6.34(2H, brs),
7.79(1H, s),
10.44(1H, brs).

EXAMPLE 19

Production of
2-Amino-9-[(1R,2R,4S,5S)-4,5-bis(benzoyloxymethyl)-2-(phenoxythiocarbonyloxy)-cyclohexyl]-6-(2-methoxyethoxy)purine In an atmosphere of argon gas, 4-dimethylaminopyridine (125.2 mg, 1.02 mmoles) and phenyloxythiocarbonyl chloride (100 μl, 0.55 mmole) were added to 2-amino-9 -[(1R,2R,4S,5S)-4,5-bis(benzoyloxymethyl)-2-hydroxycyclohexyl]-6-(2-methoxyethoxy)-purine (260 mg, 0.45 mmole) in acetonitrile (7.5 ml). The mixture was reacted at room temperature for 24 hours.

Then, 0.1M aqueous solution of sodium hydrogen carbonate was added to the reaction mixture, and the mixture was subjected to extraction with ethyl acetate. The extract solution was washed with water and then with saturated aqueous solution of sodium chloride and dried on anhydrous sodium sulfate, after which the solvent was distilled off. The residue was purified by silica gel column chromatography (methylene chloride:methanol=50:1, v/v) to obtain 2-amino-9-[(1R,2R,4S,5S)-4,5-bis(benzoyloxymethyl)-2-(phenoxythiocarbonyloxy)-cyclohexyl]-6-(2-methoxyethoxy)-purine (225.9 mg, Yield 70.3%).

NMR (200 MHzFT, TMS, CDCl$_3$) δ:
1.99–2.23(2H, m),
2.44–2.65(3H, m),
2.93(1H, m),
3.44(3H, s),
3.82(2H, t, J=5.0 Hz),
4.44–4.86(7H, m),
4.93(2h, brs),
6.27(1H, m),
6.82–7.02(2H, m),
7.18–7.67 (9H, m),
7.62(1H, s),
7.96–8.11(4H, m).

EXAMPLE 20

Production of
2-Amino-9-[(1S,3S,4S)-3,4-bis(benzoyloxymethyl)-cyclohexyl]-6-(2-methoxyethoxy)-purine In an atmosphere of argon gas, 2-amino-9-(1R,2R,4S,5S)-4,5-bis(benzoyloxymethyl)-2-(phenoxythiocarbonyloxy)-cyclohexyl]-6-(2-methoxyethoxy)-purine (100 mg, 0.14 mmole) was dissolved in anhydrous toluene (3.1 ml), and then 2,2'-azobisisobutyronitrile (49.2 mg, 0.3 mmole) and trimethyltin hydride (82 μl, 0.3 mmole) were added to the solution. After stirring the mixture at room temperature for 20 minutes, the reaction was further continued at 75° C. for 3 hours. The solvent was distilled off from the reaction mixture under reduced pressure, and the residue was purified by silica gel column chromatography (methylene chloride:methanol=50:1, v/v) to obtain 2-amino-9-[(1S,3S,4S)-3,4-bis(benzoyloxymethyl)cyclohexyl]-6-(2-methoxyethoxy)-purine (17.6 mg, Yield 22.4%).

NMR (200 MHzFT, TMS, CDCl$_3$) δ:
1.74–2.61(8H, m),
3.42(3H, s),
3.81(2H, t, J=5.0 Hz), 4.46–4.73(7H, m),
4.80(2H, brs),
7.36–7.50(4H, m),
7.52–7.63(2H, m),
7.73(1H, s),
7.98–8.10(4H, m).

EXAMPLE 21

Production of 9-[(1S,3S,4S)-3,4-Bis(hydroxymethyl)-cyclohexyl]-guanine

Anhydrous methanol (1 ml) was added to 2-amino-9-[(1S,3S,4S)-3,4-bis(benzoyloxymethyl)-cyclohexyl]-6-(2-methoxyethoxy)-purine (17.4 mg, 0.03 mmole). While cooling the mixture with ice, sodium methoxide (1.62 mg, 0.03 mmole) was added thereto, and the whole mixture was stirred at room temperature overnight. The reaction mixture was neutralized with dilute hydrochloric acid, and the solvent was distilled off under reduced pressure. Then, ethyl ether and water were added to the mixture, an ethyl ether layer was removed, and water was distilled off. The residue was heated at 100° C. for one hour together with 2N aqueous hydrochloric acid (1 ml). After neutralizing the reaction mixture with 1N solution of sodium hydroxide, the reaction mixture was subjected to Diaion HP-20 column chromatography (methanol concentration gradient) to obtain 9-[(1S,3S,4S)-3,4-bis(hydroxymethyl)-cyclohexyl]-guanine (5.7 mg, 31.3%).

NMR (200 MHzFT, TMS, DMSO-$d_6$) δ:
1.48–1.98(7H, m),
2.08(1H, m),
3.38–3.65(4H, m),
4.32(1H, m),
4.43–4.72(2H, m),
6.45(2H, brs),
7.84(1H, s),
10.57(1H, brs).

What is claimed is:

1. A nucleic acid derivative selected from the group consisting of 9-[2,3-bis(hydroxymethyl)-1-cyclopentyl]-adenine, 9-[3,4-bis(hydroxymethyl)-1-cyclohexyl]-adenine, 9-(3,4-bis(hydroxylmethyl)-1-cyclohexyl]-guanine, and any physiologically acceptable salts thereof.

2. A nucleic acid derivative selected from 9-[(1R,2R,3S)-2,3-bis(hydroxymethyl)-1-cyclopentyl]-adenine and physiologically acceptable salts thereof.

3. A pharmaceutical composition, where said composition comprises an antihepatitis compound of claim 1 as the active agent along with a pharmaceutically acceptable carrier.

* * * * *